United States Patent
Madsen et al.

(10) Patent No.: US 10,188,371 B2
(45) Date of Patent: *Jan. 29, 2019

(54) ULTRASOUND PHANTOM HAVING A CURVED SURFACE

(71) Applicant: Wisconsin Alumni Research Foundation, Madison, WI (US)

(72) Inventors: Ernest L. Madsen, Madison, WI (US); Gary R. Frank, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 806 days.

This patent is subject to a terminal disclaimer.

(21) Appl. No.: 14/514,512

(22) Filed: Oct. 15, 2014

(65) Prior Publication Data
US 2015/0059433 A1  Mar. 5, 2015

Related U.S. Application Data

(63) Continuation of application No. 13/308,662, filed on Dec. 1, 2011, now Pat. No. 8,887,552.

(51) Int. Cl.
*A61B 8/00* (2006.01)
*G01N 29/265* (2006.01)
*G01N 29/30* (2006.01)

(52) U.S. Cl.
CPC .......... *A61B 8/587* (2013.01); *G01N 29/265* (2013.01); *G01N 29/30* (2013.01)

(58) Field of Classification Search
CPC .................................................. A61B 8/587
See application file for complete search history.

(56) References Cited

U.S. PATENT DOCUMENTS

| | | | | |
|---|---|---|---|---|
| 4,808,140 A * | 2/1989 | Clavet | ................. | A63H 33/082 446/122 |
| 5,840,034 A * | 11/1998 | Amemiya | .......... | G01N 29/0609 128/916 |
| 8,887,552 B2 * | 11/2014 | Madsen | ............... | G01N 29/265 73/1.86 |
| 2002/0007897 A1 * | 1/2002 | Farley | .................... | B29C 70/24 156/163 |
| 2002/0170339 A1 * | 11/2002 | Passi | ................... | A61B 8/0875 73/1.86 |

* cited by examiner

*Primary Examiner* — Robert R Raevis
(74) *Attorney, Agent, or Firm* — Bell & Manning, LLC

(57) ABSTRACT

A phantom used in quality assurance and performance tests and/or in pre-purchase testing of ultrasound scanners is provided. The phantom includes a container, a boundary formed within the container, and a curved scanning surface. The container includes a top surface, a bottom surface opposite the top surface, and a wall mounted between the top surface and the bottom surface to form the container. The boundary is configured to hold a tissue mimicking material. The curved scanning surface is formed in the top surface in a direction towards an interior of the container. The curved scanning surface is shaped to support translation perpendicular to an image plane of an application end of an ultrasound transducer along at least a portion of an axis extending between a first location on the curved scanning surface and a second location on the curved scanning surface.

20 Claims, 15 Drawing Sheets

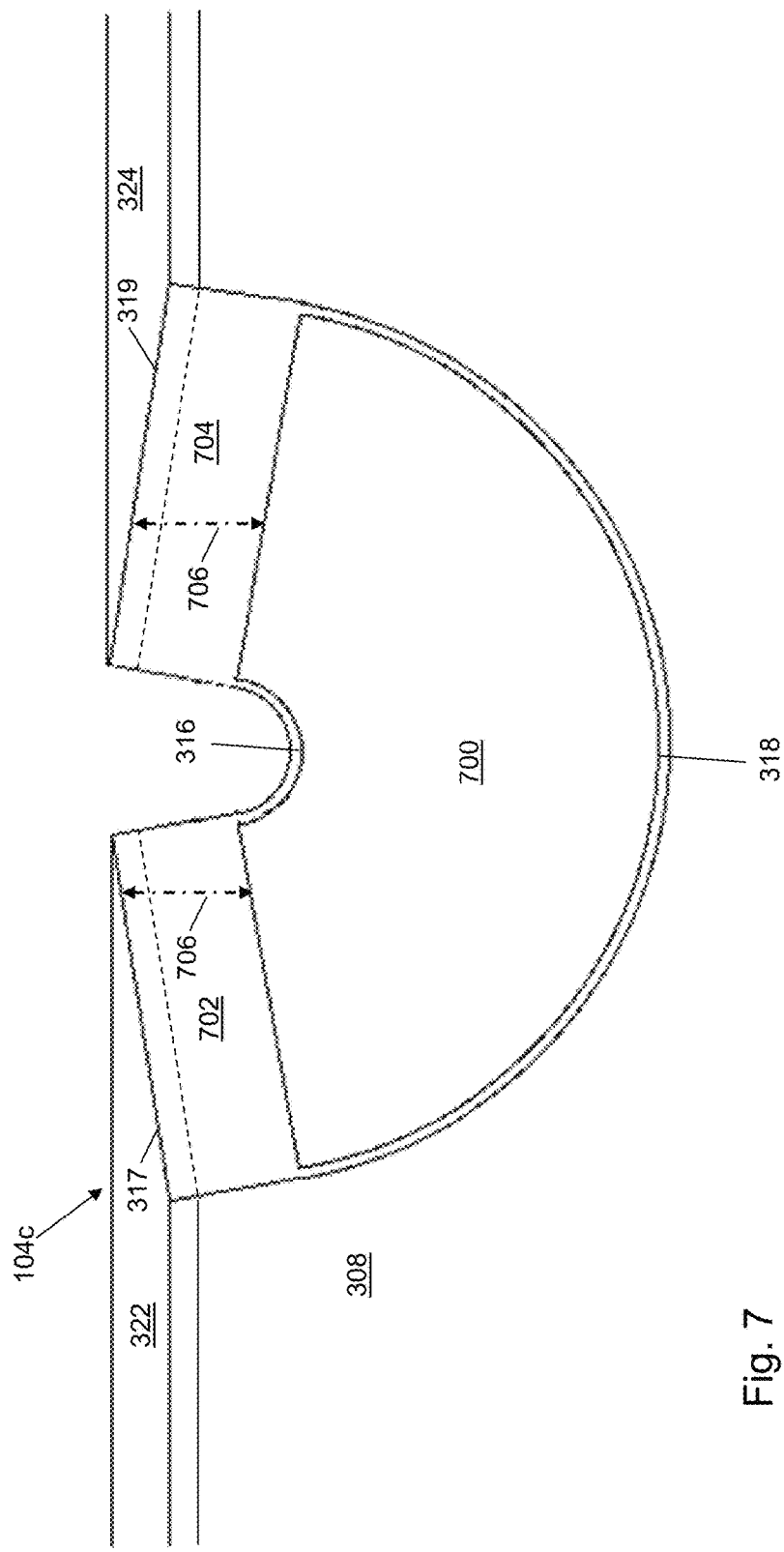

ULTRASOUND PHANTOM HAVING A CURVED SURFACE

CROSS-REFERENCE TO RELATED APPLICATIONS

The present application is a continuation of U.S. patent application Ser. No. 13/308,662 that was filed Dec. 1, 2011, the entire contents of which are hereby incorporated by reference.

REFERENCE TO GOVERNMENT RIGHTS

This invention was made with government support under CA111289, CA112192, CA140939, CA140271, and EB010098 awarded by the National Institutes of Health. The government has certain rights in the invention.

BACKGROUND

Periodic testing of ultrasound scanners and transducers is important for maintaining image quality, and is a required element of ultrasound practice accreditation programs. A new federal law, which goes into effect in 2012 in the United States, requires echocardiography imaging practices to achieve and maintain accredited status in order to be reimbursed for imaging examinations of Medicare and Medicaid patients. This new legislation, as well as similar requirements imposed by private insurance providers, has increased the focus on accreditation, and performance evaluation of medical imaging equipment including ultrasound scanners.

As understood by a person of skill in the art, there are a variety of types of phantoms used to support the quality assurance and performance testing of ultrasound scanners. Recommended tests include an element or channel failure (EOCF) test, a distance measurement accuracy (DMA) test, and a maximum depth of penetration (DOP) test. In the EOCF test, images of a macroscopically uniform phantom are inspected for the presence of shadowing extending from the transducer surface. The potential clinical significance of any detected shadowing is assessed. In the distance measurement accuracy test, the accuracy of distance measurements made in the vertical and horizontal directions using a phantom containing multiple objects is determined. In the DOP test, an assessment of the maximum depth from which echoes can be detected is measured. For example, U.S. Pat. No. 5,670,719 to Madsen, et al., discloses a phantom containing background material mimicking the ultrasonic characteristics of human tissue and coplanar spherical target lesions ultrasonically contrasting with the background material. Digitized images can be formed from the ultrasound scan of slices in which the lesions are centered. A lesion signal to noise ratio, LSNR, is calculated at each sphere in the target lesion slice. This calculation employs (1) a pixel value average calculated over a sample area of the target image slice centered at a pixel location and of a size approximately that of the cross-sectional area of the target lesions, (2) an average pixel value calculated over an averaging area centered at the same pixel coordinate, but containing mostly background image data, and (3) a standard deviation of averaged pixel values calculated in the background material image plane. The proximal and distal depth range limits of detectability of an ultrasound scanner, for a given lesion diameter and contrast, can be determined based on the number of pixel locations in a depth range of the scanned plane having an absolute value LSNR greater than a threshold value.

For quality assurance and performance testing, most phantoms contain objects to be detected that are suspended in a material that closely mimics the ultrasonic propagation characteristics of human tissue. For example, a phantom may contain metal or plastic fibers, spheres, cylinders, etc, that may be oriented in a particular direction, such as perpendicular to the scanning plane, at known locations or at random, unknown locations. For example, U.S. Pat. No. 4,843,866 to Madsen, et al., discloses a phantom including a multiplicity of scattering particles spaced sufficiently close to each other that the scanner is incapable of resolving individual scattering particles and testing spheres having a testing sphere ultrasonic speed, specific gravity, attenuation coefficient, and backscatter coefficient, at least one of which is different from the corresponding suspension material ultrasonic speed, specific gravity, attenuation coefficient, and backscatter coefficient. The testing spheres are located within the phantom in a random array.

U.S. Pat. No. 6,238,343, to Madsen, et al., discloses an ultrasound phantom configured to provide multiple testing capabilities for quality assurance on ultrasound scanners. The phantom includes a section with an array of target spheres that allow the ability of the scanner to delineate the intersection of a plane of symmetry of the scan slice with diagnostic objects to be determined. Other sections allow low contrast resolution of large objects, spatial resolution regarding lateral and axial dimensions, maximum visualization depth, image gray level uniformity, and distance measurement accuracy to be determined. The phantom may be utilized to provide comparative tests of various scanners and to monitor the performance of a particular scanner over time to determine any changes in the performance of the scanner.

Ideally, the suspension materials are capable of mimicking soft human tissue with respect to at least three characteristics: speed of sound, ultrasonic attenuation, and ultrasonic backscattering. The attenuation coefficient should be approximately proportional to the ultrasonic frequency. In other words, the variation of the attenuation coefficient with respect to frequency, or the attenuation coefficient slope, should remain constant approximately constant over a range of ultrasonic frequencies. The attenuation coefficient should extrapolate to zero as the frequency reduces to zero. These characteristics of human tissue should be maintained at all frequencies in the typical range of ultrasonic scanners, from 1 to 15 megahertz (MHz). Moreover, the variation of these characteristics within the range of room temperature should be small and the materials should be stable in time and invulnerable to reasonable environmental fluctuations.

A tissue mimicking material satisfying the above characteristics was disclosed in U.S. Pat. No. 4,277,367, to Madsen, et al., in which both the speed of sound and the ultrasonic attenuation properties could be simultaneously controlled in a mimicking material based on water based gels, such as those derived from animal hides. In one embodiment, ultrasound phantoms embodying the desired features for mimicking soft tissue were prepared from a mixture of gelatin, water, n-propanol and graphite powder, with a preservative. In another embodiment, an oil and gelatin mixture formed the basis of the tissue mimicking material.

U.S. Pat. No. 5,625,137 to Madsen, et al. discloses a tissue mimicking material with intrinsic very low acoustic backscatter coefficient that may be in liquid or solid form. A component in both the liquid and solid forms is a filtered aqueous mixture of large organic water soluble molecules and an emulsion of fatty acid esters, which may be based on a combination of milk and water. Hydroxy compounds, such as n-propanol, can be used to control the ultrasonic speed of propagation through the material.

The tissue mimicking material is enclosed in a container which includes an ultrasound transmitting window. For example, U.S. Pat. No. 6,190,915, to Madsen, et al., discloses an ultrasound transmitting window cover that seals and protects a water-based tissue mimicking material within the phantom container. The window cover includes a multi-layer film formed of at least a layer of metal adhered to a layer of plastic. The metal layer is essentially impervious to moisture and air molecules, preventing both desiccation of the water based material within the phantom and oxidation or contamination of the tissue mimicking material.

Ultrasound scanners for medical imaging are available from several manufacturers, in various models, with corresponding variations in the performance of the scanners. Additionally, each model of scanner may include one or more transducers of various shapes and sizes and having different types of sensors. For example, the transducers may include a single sensor or multiple sensor elements forming a linear or two-dimensional array, including a phased array. The types of arrays may include a linear array or an arc-shaped array (convex array). The radius of curvature (ROC) of the convex array can vary from 0.5 mm to 7 cm. The different types of arrays may operate at frequencies in the range of from 1 to 15 MHz or more.

SUMMARY

In an example embodiment, a phantom used in quality assurance and performance tests and/or in pre-purchase testing of ultrasound scanners is provided. The phantom includes, but is not limited to, a container, a boundary formed within the container, and a curved scanning surface. The container includes a top surface, a bottom surface opposite the top surface, and a wall mounted between the top surface and the bottom surface to form the container. The boundary is configured to hold a tissue mimicking material. The curved scanning surface is formed in the top surface in a direction towards an interior of the container. The curved scanning surface is shaped to support translation perpendicular to an image plane of an application end of an ultrasound transducer along at least a portion of an axis extending between a first location on the curved scanning surface and a second location on the curved scanning surface.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIG. 7 depicts a second scanning surface useable with the phantom of FIG. 3 in accordance with another alternative, illustrative embodiment.

FIG. 8b depicts a right-side schematic view of the phantom of FIG. 8a.

FIG. 8c depicts a top schematic view of the phantom of FIG. 8a.

FIG. 9b depicts a top schematic view of the third phantom of FIG. 9a.

FIG. 10b depicts a top schematic view of the fourth phantom of FIG. 10a.

FIG. 11 is an image taken using a transducer, such as that illustrated in FIG. 2, with the phantom of FIG. 9a.

DETAILED DESCRIPTION

Figure 1:
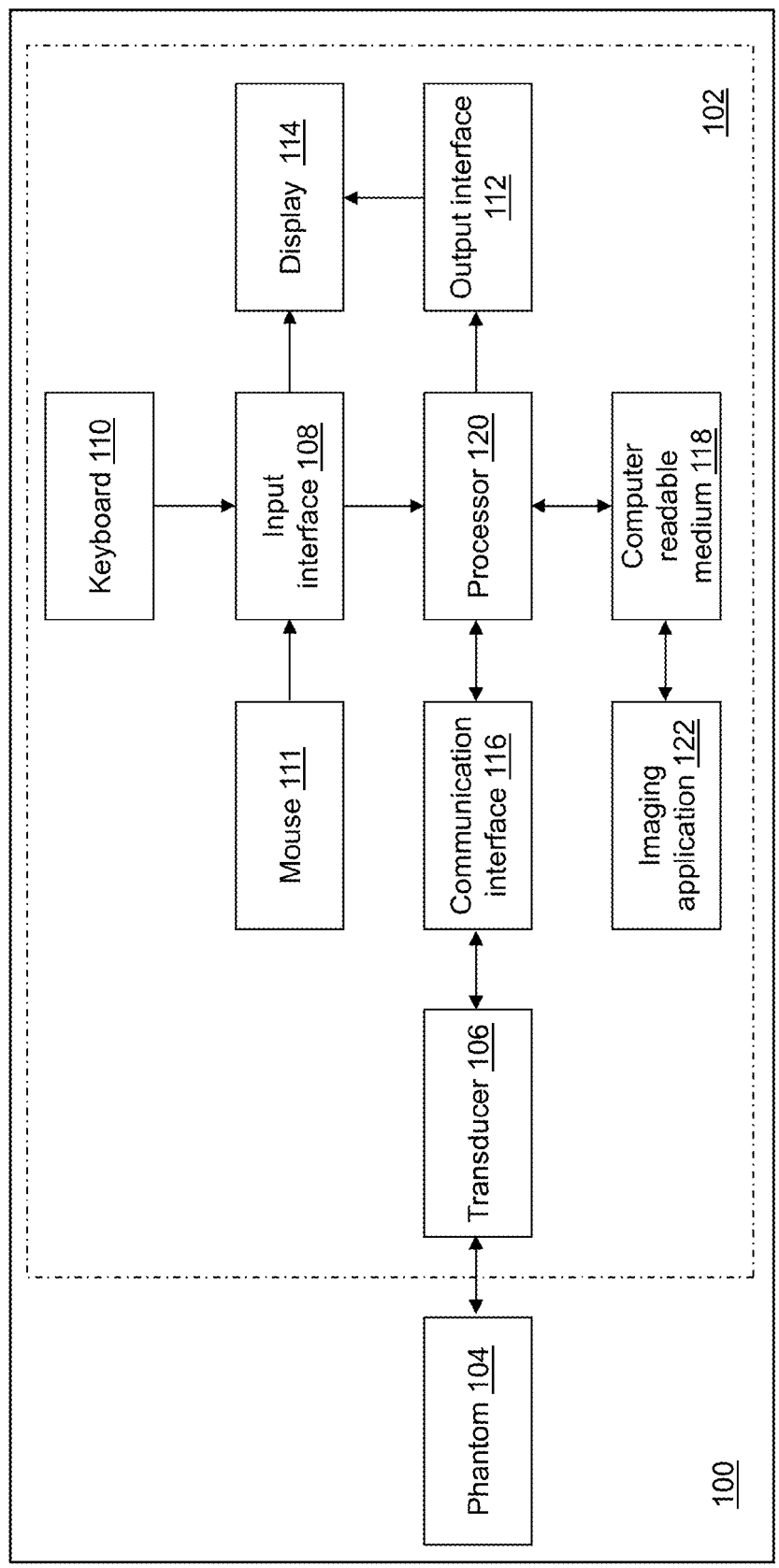
FIG. 1 depicts a block diagram of an ultrasound testing system in accordance with an illustrative embodiment.

With reference to FIG. 1, a block diagram of an ultrasound testing system 100 is shown in accordance with an illustrative embodiment. In the illustrative embodiment, ultrasound testing system 100 may include an ultrasound 102 and a phantom 104. Ultrasound 102 may include a transducer 106, an input interface 108, a keyboard 110, a mouse 111, an output interface 112, a display 114, a communication interface 116, a computer-readable medium 118, a processor 120, and an imaging application 122. Different and additional components may be incorporated into ultrasound 102. For example, ultrasound 102 may be connected to a printer or second computer readable media such as a compact disk (CD), digital versatile disk (DVD), a smart card, a flash memory device, etc. through output interface 112, communication interface 116, and/or input interface 108.

Ultrasound 102 further may be connected directly or indirectly to a database or other data processing system that receives imaging data from ultrasound 102. For example, ultrasound 102 may be connected using communication interface 116 through a network to a database that stores the imaging data for archival or additional analysis purposes. The network may include one or more networks of the same or different types that may be a wired and/or a wireless public or private network including a cellular network, a local area network, a wide area network such as the Internet, etc. The network further may be comprised of sub-networks and consist of any number of devices.

Ultrasound 102 may be connected to one or more transducers of different types. Transducer 106 transmits ultrasound pulses at frequencies generally in the range of one to fifteen MHz into phantom 104 and receives echoes from objects contained within phantom 104. Transducer 106 may have various shapes and sizes and include various types of sensors. For example, transducer 106 may include a single sensor or multiple sensor elements forming a linear or two-dimensional array, including a phased array. The types of arrays may include a high-frequency linear array, a lower frequency linear array, a low frequency curvilinear sector/ vector array, a tightly-curved array, etc.

Input interface 108 provides an interface for receiving information from the user for entry into ultrasound 102 as known to those skilled in the art. Input interface 108 may provide a wired or wireless electronic interface to various input technologies including, but not limited to, keyboard 110, a pen and touch screen, mouse 111, a track ball, a touch screen, a keypad, one or more buttons, etc. to allow the user to enter information into ultrasound 102 or to make selections presented in a user interface displayed on display 114. The same interface may support both input interface 108 and output interface 112. For example, a touch screen both allows user input and presents output to the user. Ultrasound 102 may have one or more input interfaces that use the same or a different input interface technology. Mouse 111, keyboard 110, and/or display 114 and other input technologies further may be accessible to ultrasound 102 through communication interface 116.

Output interface 112 provides an interface for outputting information for review by a user of ultrasound 102. For example, output interface 112 may include a wired or wireless electronic interface to display 114, a speaker, a printer, etc. Display 114 may be a thin film transistor display, a light emitting diode display, a liquid crystal display, or any of a variety of different displays known to those skilled in the art. Ultrasound 102 may have one or more output interfaces that use the same or a different interface technology. Display 114 and other output technologies further may be accessible to ultrasound 102 through communication interface 116.

Communication interface 116 provides an interface for receiving and transmitting data between devices using various protocols, transmission technologies, and media as known to those skilled in the art. Communication interface 116 may support communication using various transmission media that may be wired or wireless. Ultrasound 102 may have one or more communication interfaces that use the same or a different communication interface technology. Data and messages may be transferred between transducer 106 and processor 120 using communication interface 116.

Computer-readable medium 118 is an electronic holding place or storage for information so that the information can be accessed by processor 120 as known to those skilled in the art. Computer-readable medium 118 can include, but is not limited to, any type of random access memory (RAM), any type of read only memory (ROM), any type of flash memory, etc. such as magnetic storage devices (e.g., hard disk, floppy disk, magnetic strips, . . . ), optical disks (e.g., CD, DVD, . . . ), smart cards, flash memory devices, etc. Ultrasound 102 may have one or more computer-readable media that use the same or a different memory media technology. Ultrasound 102 also may have one or more drives that support the loading of a memory media such as a CD or DVD. Computer-readable medium 118 may provide the electronic storage medium for the database.

Processor 120 executes instructions as known to those skilled in the art. The instructions may be carried out by a special purpose computer, logic circuits, or hardware circuits. Thus, processor 120 may be implemented in hardware, firmware, or any combination of these methods and/or in combination with software. The term "execution" is the process of running an application or the carrying out of the operation called for by an instruction. The instructions may be written using one or more programming language, scripting language, assembly language, etc. Processor 120 executes an instruction, meaning that it performs/controls the operations called for by that instruction. Processor 120 operably couples with output interface 112, with input interface 108, with computer-readable medium 118, and with communication interface 116 to receive, to send, and to process information. Processor 120 may retrieve a set of instructions from a permanent memory device and copy the instructions in an executable form to a temporary memory device that is generally some form of RAM. Ultrasound 102 may include a plurality of processors that use the same or a different processing technology.

Imaging application 122 performs operations associated with creating ultrasound images based on data received from transducer 106. Imaging application 122 may be written using one or more programming languages, assembly languages, scripting languages, etc. as understood by a person of skill in the art.

Figure 2:
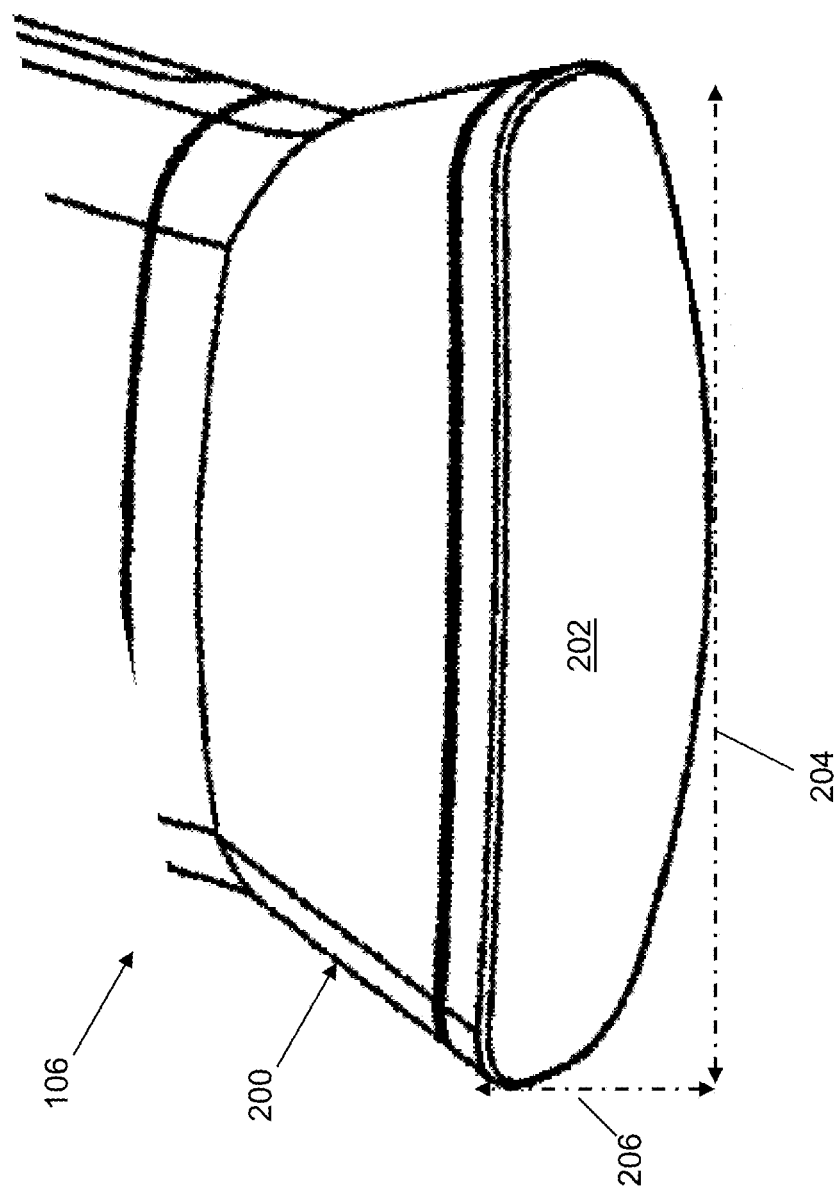
FIG. 2 depicts an application end of a transducer of the ultrasound testing system of FIG. 1 in accordance with an illustrative embodiment.

With reference to FIG. 2, an application end 200 of transducer 106 is shown in accordance with an illustrative embodiment. In use, application end 200 of transducer 106 is pressed against an object to be scanned using ultrasound 102. For testing and possibly training purposes, application end 200 of transducer 106 is pressed against one or more surfaces of phantom 104. In the illustrative embodiment, application end 200 includes a curved surface 202 having a width 204 and a height 206. Curved surface 202 has associated therewith a radius of curvature. Different types of transducers may have different widths, heights, and radii of curvature including those having a non-curved or flat surface. Phantom 104 is designed for use with essentially any type of transducer 106. Transducers currently in use have radii of curvature in the range of 0.5 centimeters (cm) to 7 cm though this is not intended to limit the design of phantom 104, which can be modified according to the principles disclosed herein, to accommodate smaller or larger radii of curvature and transducer sizes.

Figure 3:
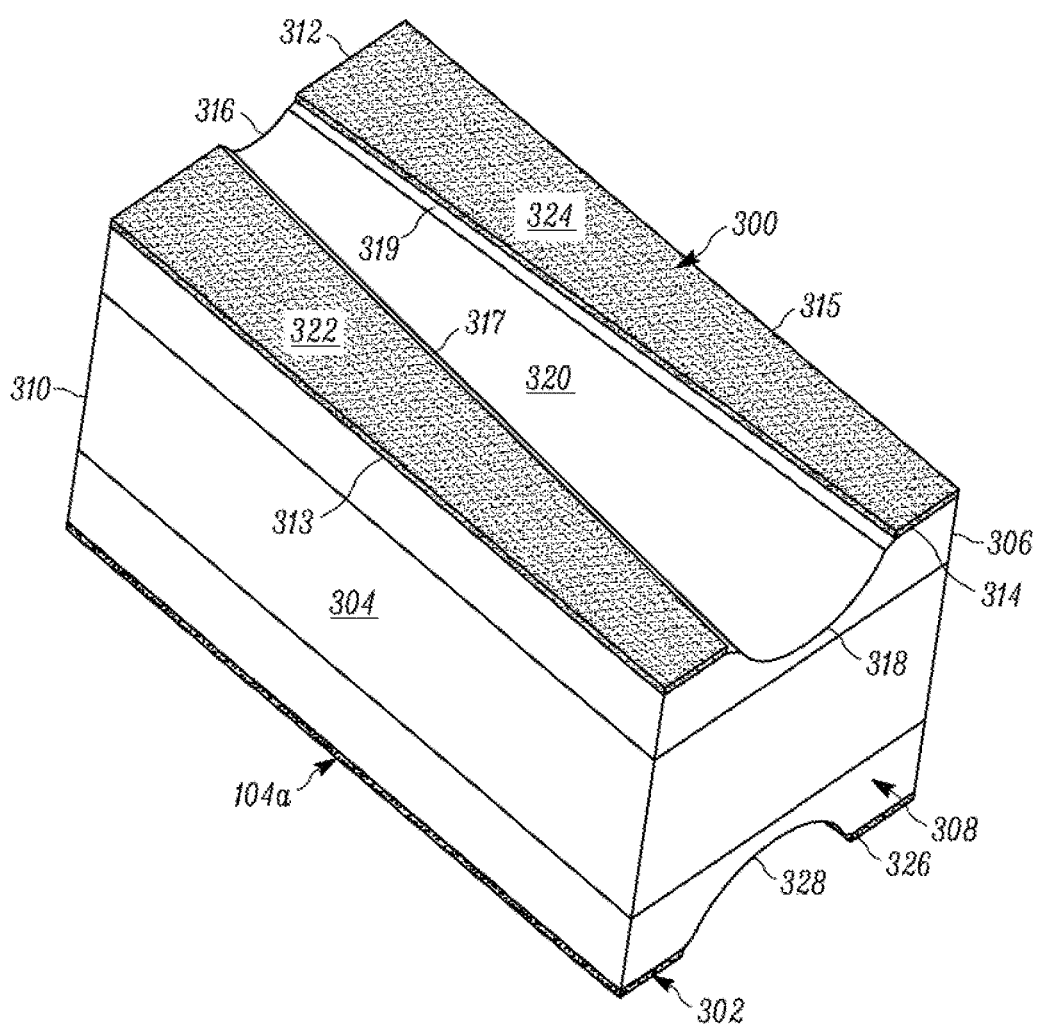
FIG. 3 is a photograph of a phantom for use in the ultrasound testing system of FIG. 1 in accordance with an illustrative embodiment.

With reference to FIG. 3, a photograph of a first phantom 104a is shown in accordance with an illustrative embodiment. First phantom 104a may include a top surface 300, a bottom surface 302, a right side surface 304, a left side surface 306, a front surface 308, and a back surface 310, which generally form a rectangular container though other polygonal, circular, elliptical, etc. shapes may be used. Thus, first phantom 104a includes top surface 300, bottom surface 302, and a wall mounted between top surface 300 and bottom surface 302 to form the container. The wall may have a variety of shapes and, for illustration, includes right side surface 304, left side surface 306, front surface 308, and back surface 310. Use of directional terms, such as top, bottom, right, left, front, back, etc. are merely intended to facilitate reference to the various surfaces that form first phantom 104a and are not intended to be limiting in any manner. Top surface 300 may include a first edge 312, a second edge 314, a third edge 313, and a fourth edge 315. First edge 312 is formed to delineate a transition between top surface 300 and back surface 310. Second edge 314 is formed to delineate a transition between top surface 300 and front surface 308, and is thus, generally opposite first edge 312. Third edge 313 is formed to delineate a transition between top surface 300 and right side surface 304. Fourth edge 315 is formed to delineate a transition between top surface 300 and left side surface 306, and is thus, generally opposite third edge 313.

A first curved edge 316 is formed in first edge 312 to have a first radius of curvature, where first curved edge 316 (and any other curved edge or surface referenced herein) may be circular, elliptical, parabolic, etc. The first radius of curvature is defined in a plane approximately perpendicular to top surface 300 and approximately parallel to back surface 310 and is determined based on the osculating circle formed to fit first curved edge 316 at the point most distant from top surface 300. A second curved edge 318 is formed in second edge 314 to have a second radius of curvature that is defined in a plane approximately perpendicular to top surface 300 and approximately parallel to front surface 308 and similarly is determined based on the osculating circle formed to fit second curved edge 318 at the point most distant from top surface 300.

A first curved surface 320 is formed in top surface 300 between first curved edge 316 and second curved edge 318. First curved surface 320 further includes a first bounding edge 317 and a second bounding edge 319 in top surface 300. Top surface 300 further includes a first flat surface 322 and a second flat surface 324 though first flat surface 322 and second flat surface 324 need not be flat. First flat surface 322 forms the surface between first edge 312, first bounding edge 317, second edge 314, and third edge 313. Second flat surface 324 forms the surface between first edge 312, second bounding edge 319, second edge 314, and fourth edge 315. In the illustrative embodiment, the curved edges are arcs or approximately arcs, and the angle subtended may be as large as 180°.

Bottom surface 302 may include a second curved surface (not shown) shaped in a similar manner though including a different range of radii of curvature. For example, the second curved surface may include a third curved edge 328 formed in a fifth edge 326 and a fourth curved edge 404 formed in a sixth edge 402 (shown with reference to FIG. 4). Fifth edge 326 is formed to delineate a transition between bottom surface 302 and front surface 308. Sixth edge 402 is formed to delineate a transition between bottom surface 302 and front surface 310, and is thus, generally opposite fifth edge 326.

First curved surface 320 and the second curved surface are curved so that the entire radiating surface of transducer 106 (i.e., curved surface 202) maintains contact as transducer 106 is moved over first curved surface 320 and/or the second curved surface. Differently shaped and sized transducers may be used with different portions of first curved surface 320 and/or the second curved surface. The range of radii of curvature of first curved surface 320 and the second curved surface may include the range from approximately 0.5 cm to 7 cm or more or various subsets thereof. For example, first curved edge 316 may have a radius of curvature of 1.25 cm, second curved edge 318 may have a radius of curvature of 3.5 cm, third curved edge 328 may have a radius of curvature of 3 cm, and fourth curved edge 404 may have a radius of curvature of 6.5 cm in an illustrative embodiment. In an illustrative embodiment, first curved surface 320 and/or the second curved surface are formed of a portion of a right circular cone.

Figure 4:
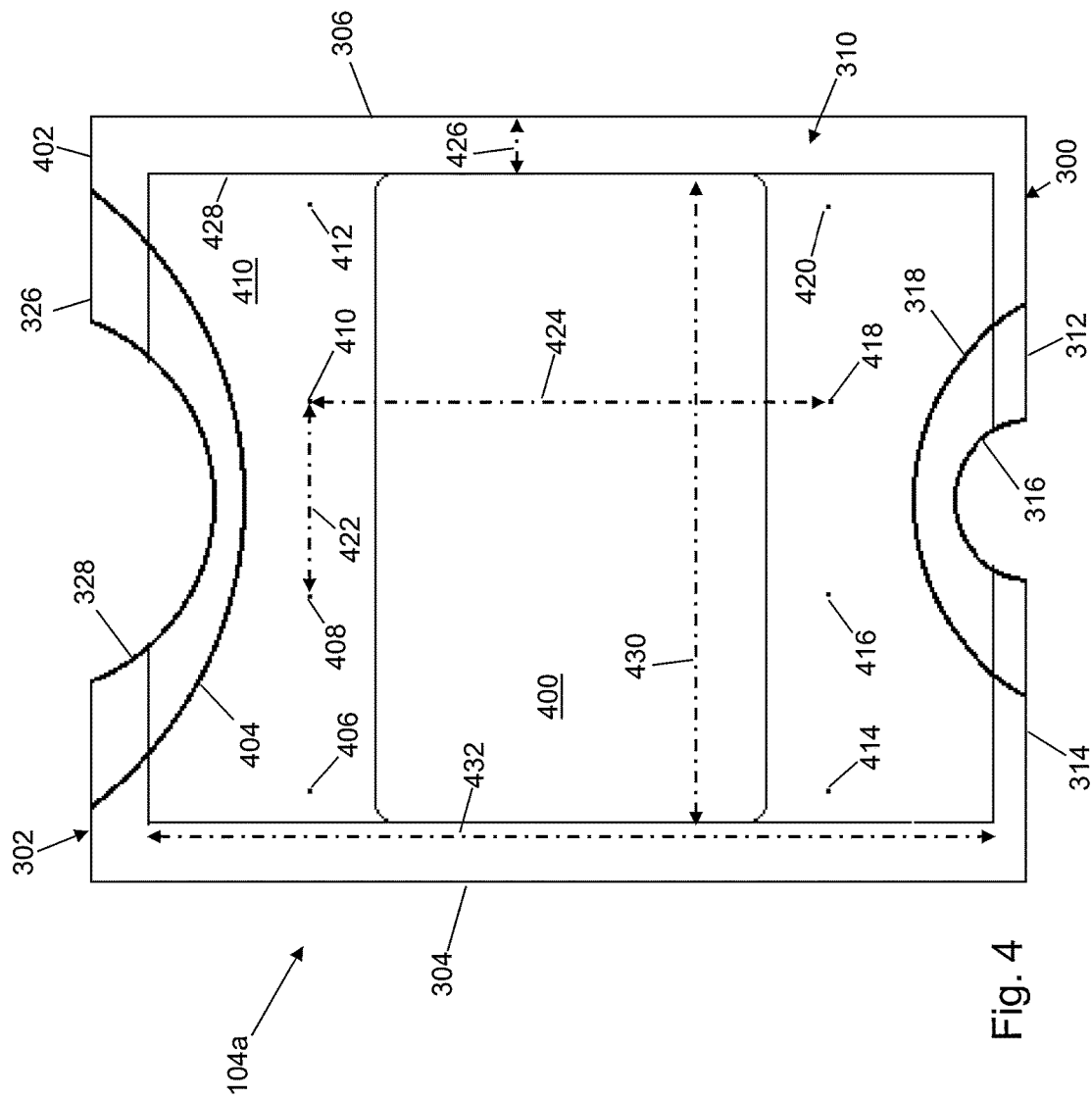
FIG. 4 depicts a back schematic view of the phantom of FIG. 3 in accordance with an illustrative embodiment.

With reference to FIG. 4, a back schematic view of first phantom 104a is shown in accordance with an illustrative embodiment. In the illustrative embodiment, first phantom 104a further may include a planar scanning window 400 mounted within back surface 310. First phantom 104a further may include a second planar scanning window 400 mounted in front surface 308 without limitation. Thus, first phantom 104a may include one or more planar scanning windows which are mounted in either or both of front surface 308 and back surface 310. As used in this disclosure, the term "mount" includes join, unite, connect, associate, insert, hang, hold, affix, attach, fasten, bind, paste, secure, bolt, screw, rivet, solder, weld, glue, mold, thermoform, couple, etc. The phrases "mounted on" and "mounted to" include any interior or exterior portion of the support member referenced. Additionally, use of the term "mount" may indicate a direct or an indirect connection between the described components/devices.

First phantom 104a further may include a plurality of fibers suspended therein. The number and arrangement of the plurality of fibers may be selected based on the type of ultrasound test to be performed using first phantom 104a and the type of transducer 106 used with ultrasound 102. For example, the plurality of fibers could be parallel with known distances between them. The accuracy with which those distances are measured using an ultrasound image is a test of the ultrasound/transducer combination. If curved surface 202 of transducer 106 is not in direct contact with the scanning window, such as first curved surface 320, and water or some other liquid separates part of first curved surface 320 from transducer 106, a distance measurement error can occur due to refraction at the liquid-to-curved surface interface.

In the illustrative embodiment of FIG. 4, first phantom 104a includes a first fiber 406, a second fiber 408, a third fiber 410, a fourth fiber 412, a fifth fiber 414, a sixth fiber 416, a seventh fiber 418, and an eighth fiber 420. First fiber 406, second fiber 408, third fiber 410, fourth fiber 412, fifth fiber 414, sixth fiber 416, seventh fiber 418, and eighth fiber 420 are arranged in a grid comprised of two rows of four fibers each. First fiber 406, second fiber 408, third fiber 410, fourth fiber 412 form a first row closest to bottom surface 302. Fifth fiber 414, sixth fiber 416, seventh fiber 418, and eighth fiber 420 form a second row closest to top surface 300. First fiber 406, second fiber 408, third fiber 410, fourth fiber 412, fifth fiber 414, sixth fiber 416, seventh fiber 418, and eighth fiber 420 extend in a direction generally parallel to top surface 300 and bottom surface 302. Within a row, the fibers are separated by a horizontal distance 422. The two rows are separated by a vertical distance 424. Merely for illustration, horizontal distance 422 may be 3 cm, vertical distance 424 may be 8 cm, and the fibers may be formed of 0.1 mm strands of nylon.

When positioned on planar scanning window 400, transducer 106 scans in a direction parallel to the plurality of fibers. Planar scanning window 400 may be formed of a plastic-coated aluminum foil (PCAF) such as that described in U.S. Pat. No. 6,190,915, to Madsen, et al. First curved surface 320 and the second curved surface further may be formed of the PCAF material. Merely for illustration, planar scanning window 400 may 6 cm in the vertical direction and 10 cm in the horizontal direction.

The remaining portions of top surface 300, bottom surface 302, right side surface 304, left side surface 306, front surface 308, and back surface 310 may be formed of any suitable material(s) that can structurally hold a tissue mimicking material within first phantom 104a without substantial transmission of water vapor or air molecules therethrough. Example materials include acrylic plastic or ABS plastic. A variety of tissue mimicking materials may be used as understood by a person of skill in the art.

First phantom 104a may be formed by mounting top surface 300, bottom surface 302, right side surface 304, left side surface 306, front surface 308, and back surface 310 together using various methods or by one piece molding the surfaces together. A boundary 428 defines a transition between top surface 300, bottom surface 302, right side surface 304, left side surface 306, front surface 308, and back surface 310 and the tissue mimicking material. As a result, top surface 300, bottom surface 302, right side surface 304, left side surface 306, front surface 308, and back surface 310 may have various widths 426 and may be formed of one or more layers of material. For illustration, width 426 may be approximately one cm. A width 430 defined by boundary 428 in the vertical direction may be approximately ten cm. A length 432 defined by boundary 428 in the horizontal direction may be approximately 13 cm.

Figure 5:
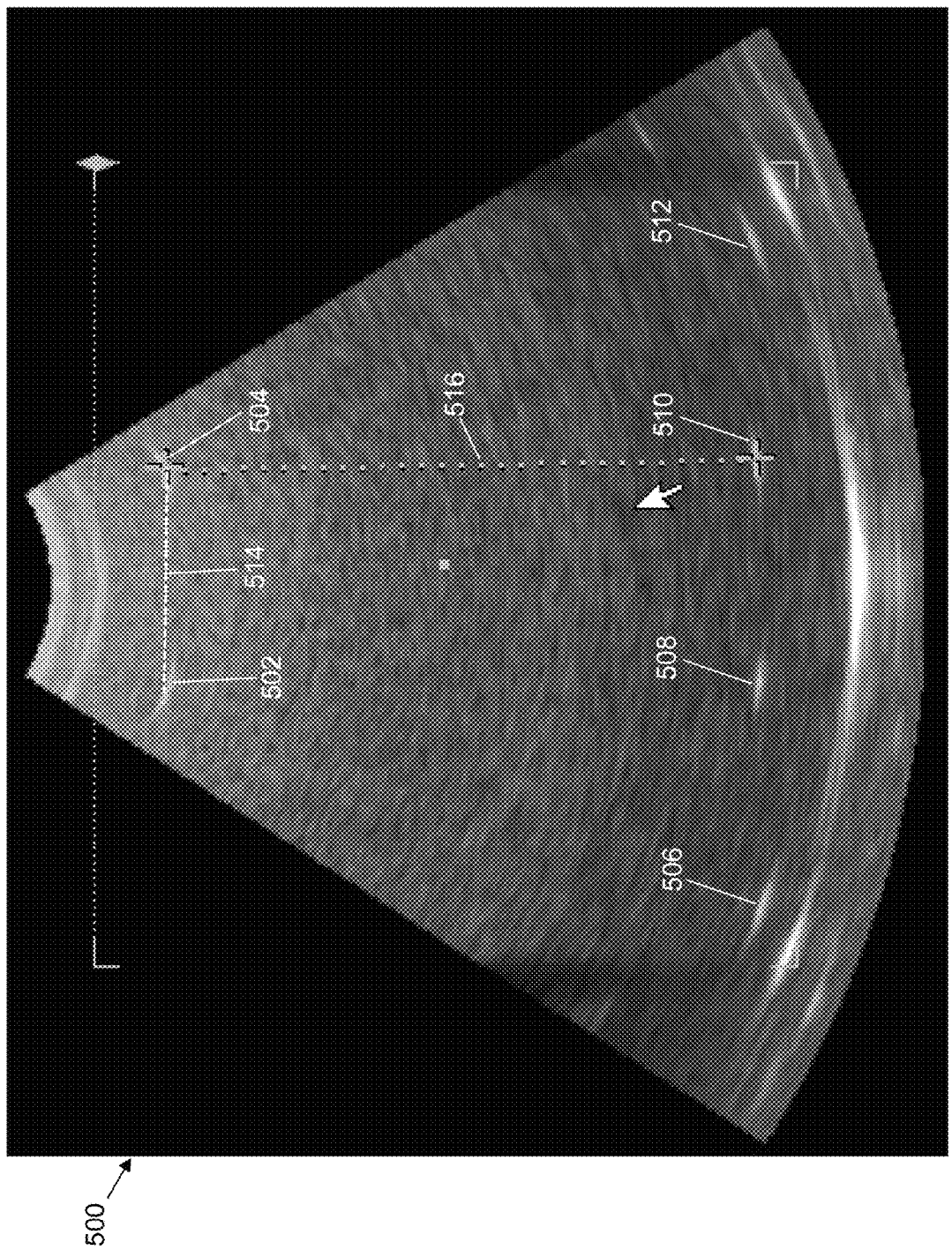
FIG. 5 is an image corresponding to a sector scan taken using a transducer, such as that illustrated in FIG. 2, with the phantom of FIG. 3.

With reference to FIG. 5, an image 500 corresponding to a sector scan is shown based on use of first phantom 104a for a distance measurement accuracy determination using the mechanical sweep of transducer 106 including a three-dimensional (3D) convex array. The mechanical scan direction is about an axis approximately connecting a center of curvature of first curved edge 316 and a center of curvature of second curved edge 318. Image 500 corresponds to an image plane approximately parallel to back surface 310 and front surface 308 and perpendicular to fibers 406, 408, 410, 412, 414, 416, 418 and 420. Images 502, 504, 506, 508, 510, and 512 of six of the eight parallel fibers of first phantom 104a are shown in image 500. The actual distance between adjacent fibers in each row was 3 cm, and the distance between the rows was 8 cm as illustrated with reference to FIG. 4. The ultrasound scanner calculated the distances to be 3.06 cm and 8 cm, which is approximately equal to or equal to the actual values.

Figure 6A:
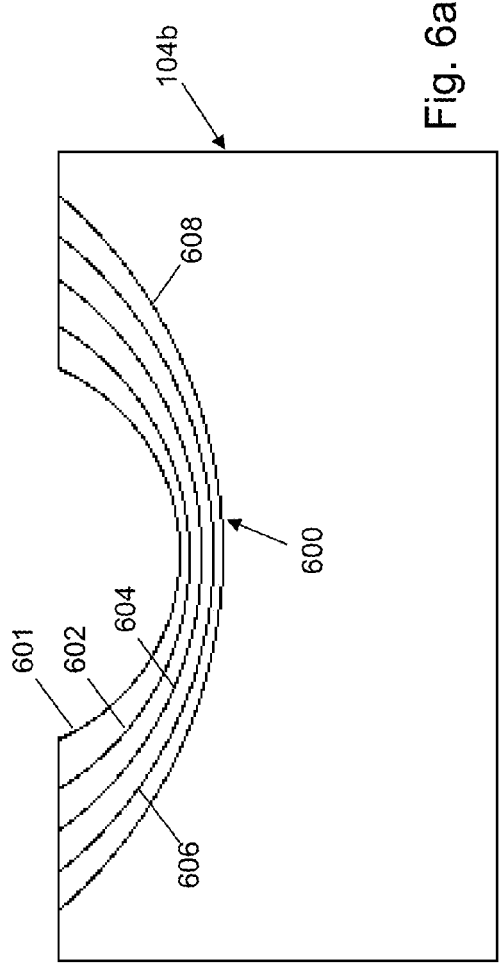
FIGS. 6a and 6b depict a stepped scanning surface useable with the phantom of FIG. 3 in accordance with an alternative, illustrative embodiment.
Figure 6B:
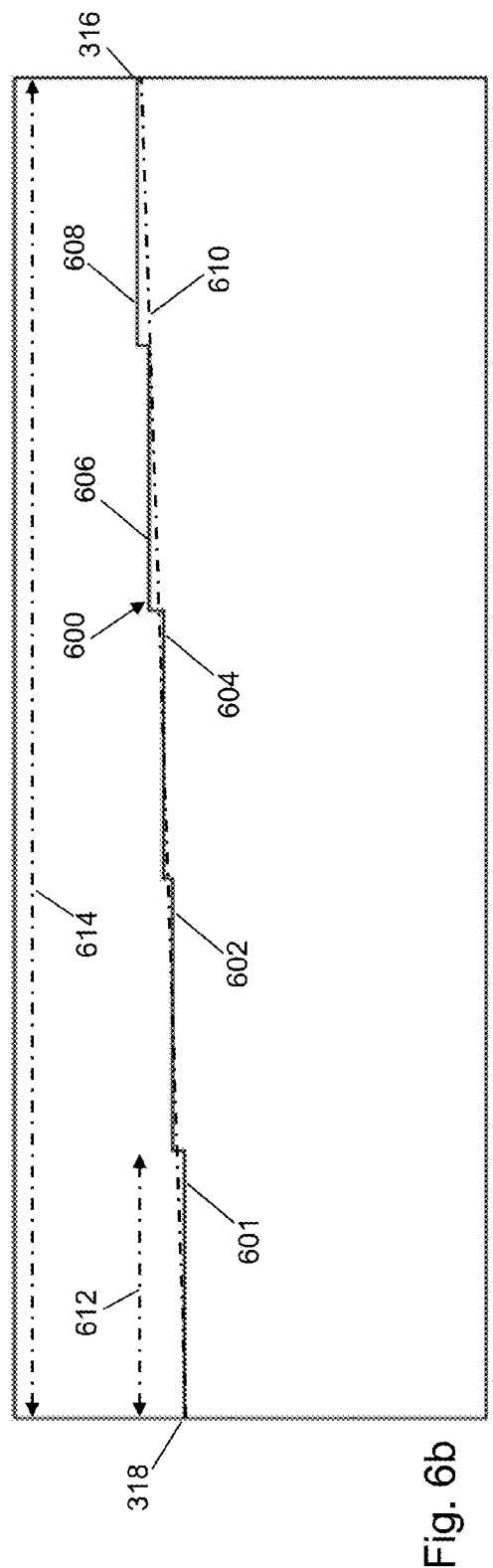

With reference to FIGS. 6a and 6b, a stepped scanning surface 600 is shown in an example second phantom 104b. Second phantom 104b may be otherwise structurally similar to first phantom 104a. Instead of the continuously varying surface 610 of first curved surface 320 as included in FIG. 6b for comparison, stepped scanning surface 600 varies in steps between the center of first curved edge 316 and the center of second curved edge 318. In the illustrative embodiment of FIGS. 6a and 6b, stepped scanning surface 600 includes a first step 601, a second step 602, a third step 604, a fourth step 606, and a fifth step 608. Merely for illustration, first step 601 has a radius of curvature of 7 cm, second step 602 has a radius of curvature of 6 cm, third step 604 has a radius of curvature of 5 cm, fourth step 606 has a radius of curvature of 4 cm, and fifth step 608 has a radius of curvature of 3 cm. Merely for illustration, a width 612 of each of first step 601, second step 602, third step 604, fourth step 606, and fifth step 608 may be equal and may be selected as 4 cm defining a total length 614 of stepped scanning surface 600 of 20 cm. First step 601, second step 602, third step 604, fourth step 606, and fifth step 608 may be formed in any order between first curved edge 316 and second curved edge 318. Also, the axes of rotation defining the surfaces of first step 601, second step 602, third step 604, fourth step 606, and fifth step 608 need not be coaxial. Second phantom 104b may be filled with materials that do not mimic tissues well in ultrasonic properties—such as polyurethane or silicone.

With reference to FIG. 7, a recessed scanning surface 700 is shown in an example third phantom 104c. Third phantom 104c may be otherwise structurally similar to first phantom 104a. Instead of first curved surface 320 extending along the entire surface between first flat surface 322 and second flat surface 324, recessed scanning surface 700 extends between a first flat portion 702 and a second flat portion 704. First flat portion 702 extends down from first bounding edge 317 and second flat portion 704 extends down from second bounding edge 319. First flat portion 702 and second flat portion 704 form flat extensions from recessed scanning surface 700 providing up to a 170 degree sector angle. In the illustrative embodiment of FIG. 7, first curved edge 316 has a 0.5 cm radius of curvature and second curved edge 318 has a 3.5 cm radius of curvature. A width 706 of first curved portion 702 and second curved portion 704 may be 1 cm.

Figure 8A:
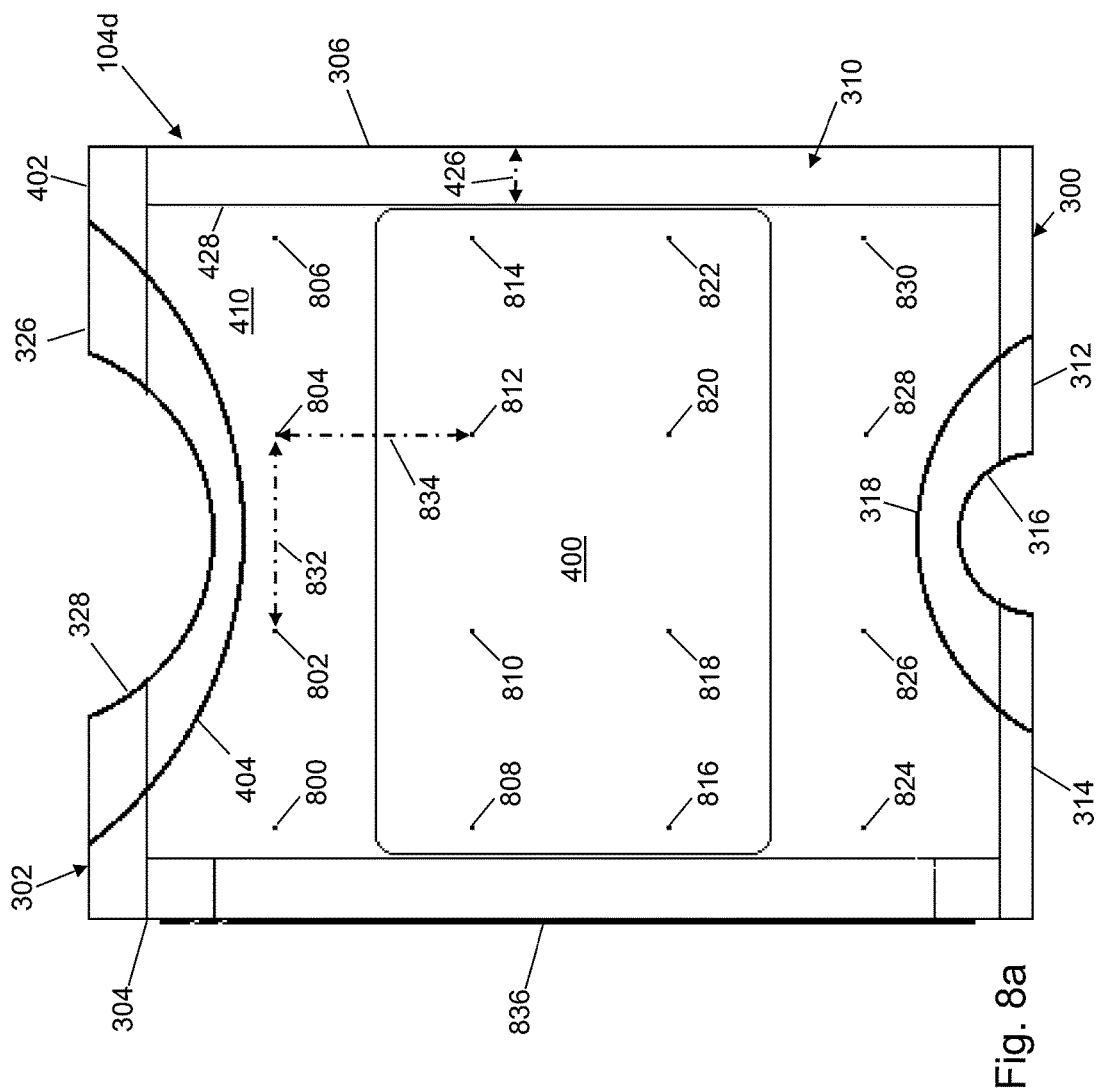
FIG. 8a depicts a back schematic view of the phantom of FIG. 3 in accordance with a second illustrative embodiment.
Figure 8B:
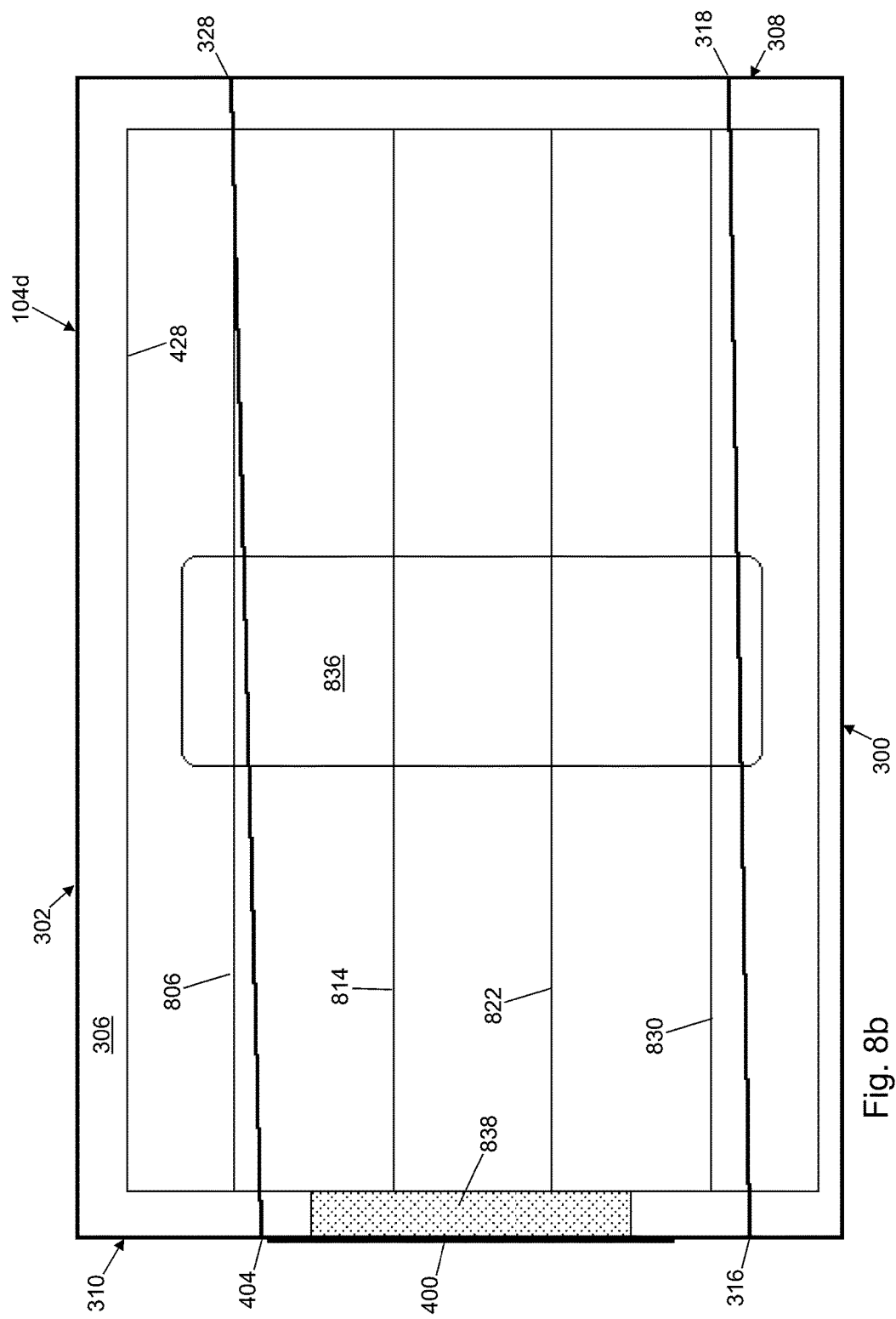
Figure 8C:
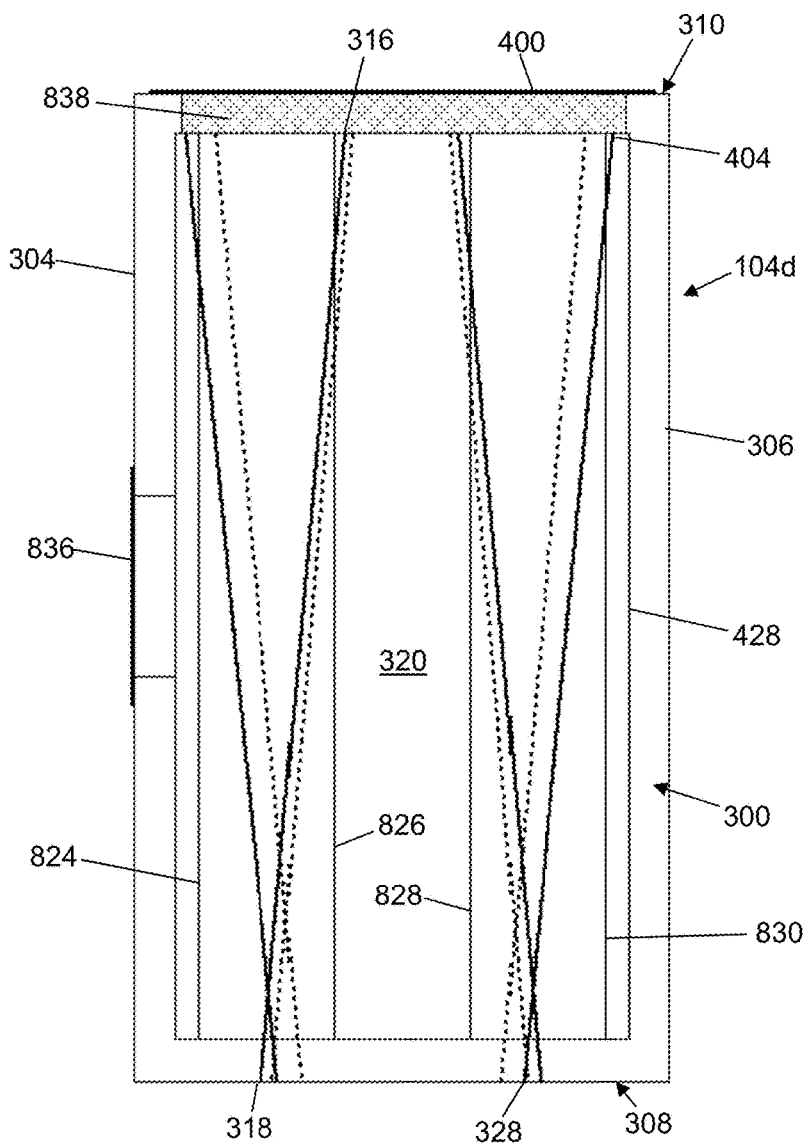

With reference to FIGS. 8a-8c, a fourth phantom 104d is shown in accordance with a second illustrative embodiment. Fourth phantom 104d is structurally similar to first phantom 104a. Instead of eight fibers arranged in two rows of four fibers each, however, fourth phantom 104d includes 16 fibers arranged to form a grid of four rows with four fibers in each row. Thus, in the illustrative embodiment of FIGS. 8a-8c, fourth phantom 104d includes a first fiber 800, a second fiber 802, a third fiber 804, a fourth fiber 806, a fifth fiber 808, a sixth fiber 810, a seventh fiber 812, an eighth fiber 814, a ninth fiber 816, a tenth fiber 818, an eleventh fiber 820, a twelfth fiber 822, a thirteenth fiber 824, a fourteenth fiber 826, a fifteenth fiber 828, and a sixteenth fiber 430. Within a row, the fibers are separated by a second horizontal distance 832. The four rows are separated by a second vertical distance 834. Merely for illustration, second horizontal distance 832 may be 3 cm, second vertical distance 834 may be 3 cm, and the fibers may be formed of 0.1 mm strands of nylon.

Fourth phantom 104d further includes a flat perpendicular scanning window 836 mounted in right side surface 304 without limitation. Thus, fourth phantom 104d may include one or more perpendicular scanning windows which are mounted in either or both of right side surface 304 and left side surface 306. When positioned on perpendicular scanning window 836, transducer 106 scans in a plane perpendicular to the plurality of fibers. Flat perpendicular scanning window 836 may be formed of the PCAF material. Merely for illustration, perpendicular scanning window 836 may 11 cm in the vertical direction and 4 cm in the horizontal direction.

With reference to FIGS. 8b and 8c, a volume 838 may be positioned between planar scanning window 400 and boundary 428. Volume 838 may be filled with the same or a different tissue mimicking material as that contained within boundary 428. For illustration, volume 838 may be 1 cm thick between planar scanning window 400 and boundary 428.

Figure 9A:
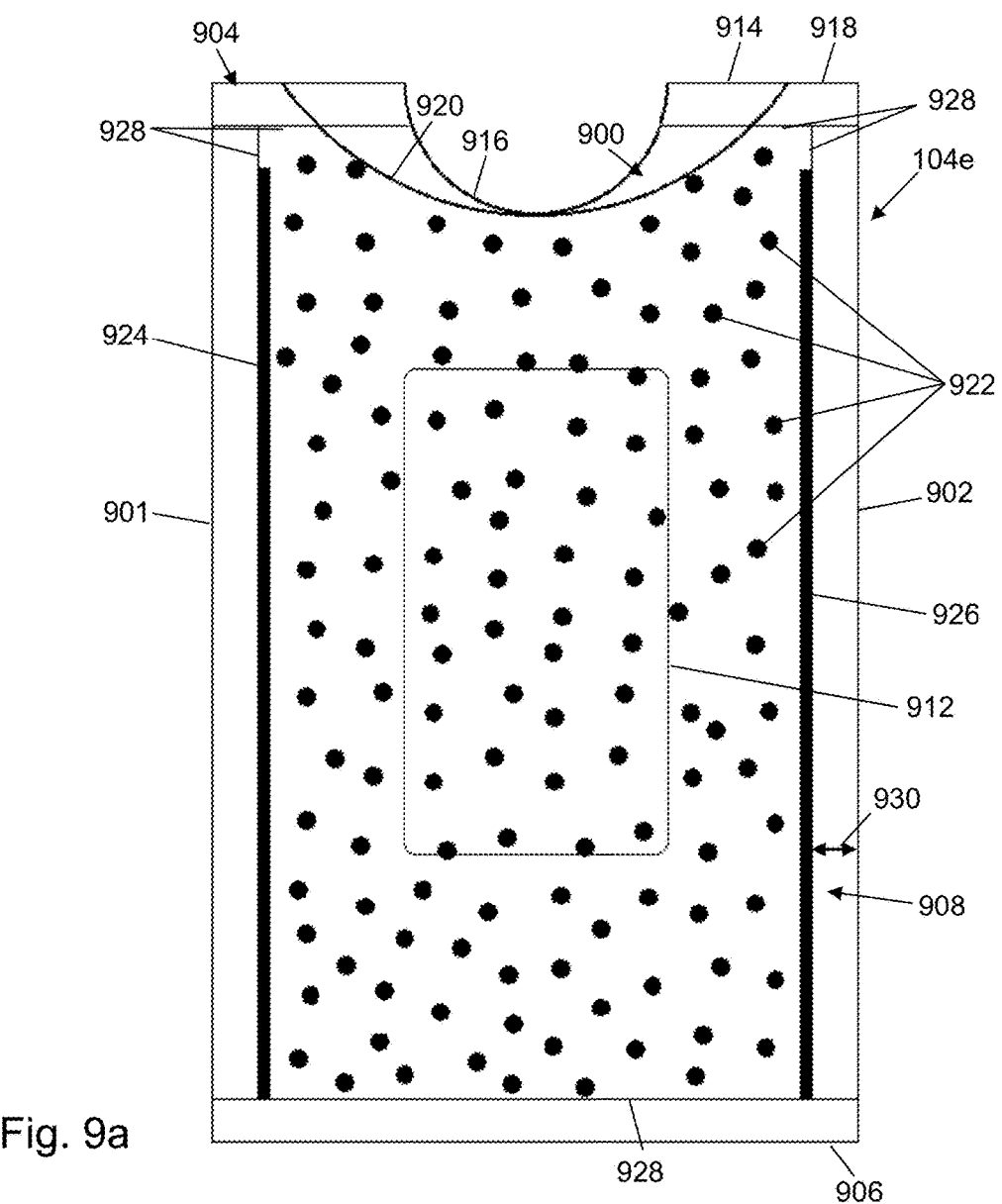
FIG. 9a depicts a front schematic view of a third phantom for use with the ultrasound system of FIG. 1 in accordance with a third illustrative embodiment.
Figure 9B:
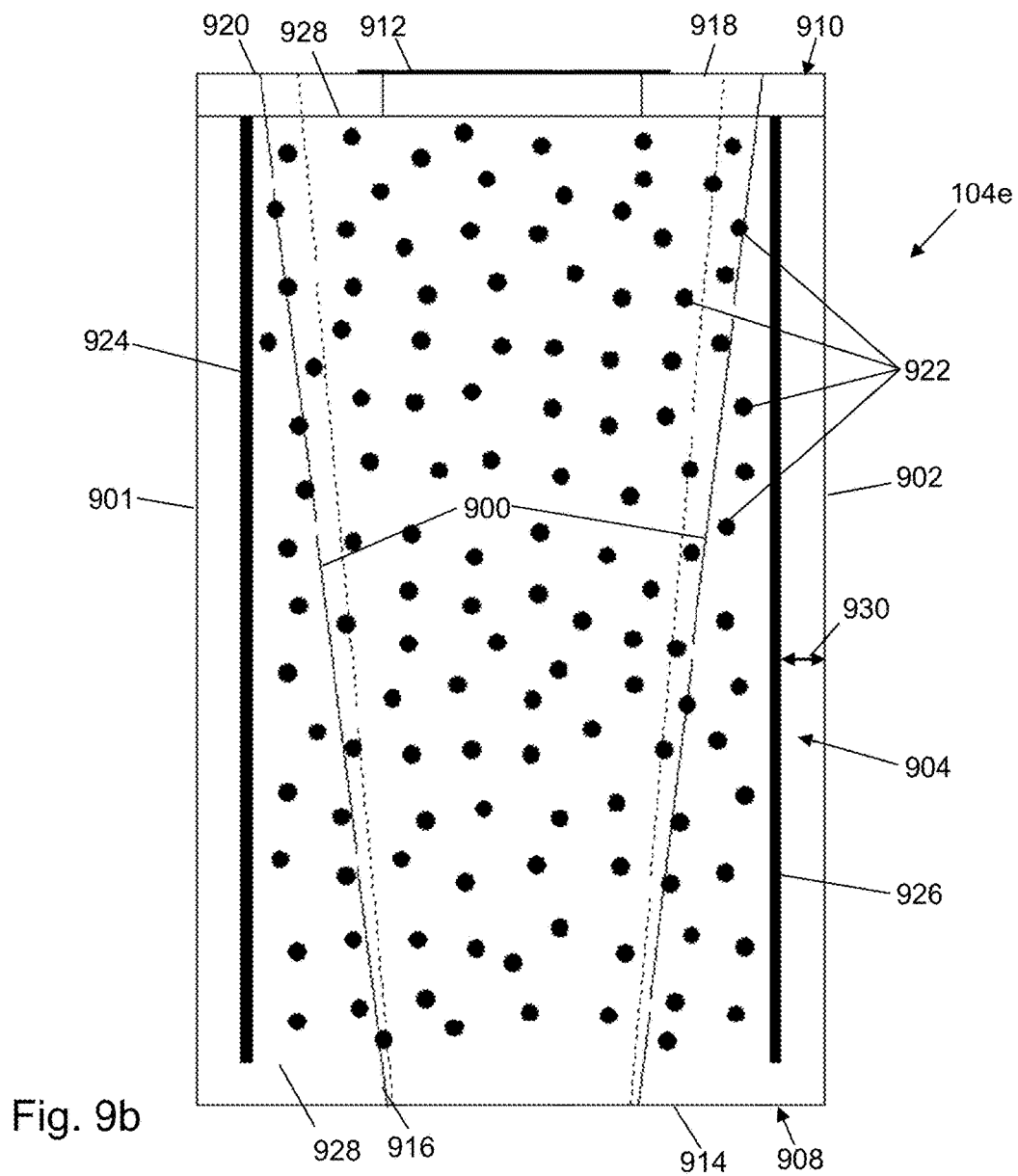

With reference to FIGS. 9a-9b, a fifth phantom 104e is shown in accordance with a third illustrative embodiment. Fifth phantom 104e is structurally similar to first phantom 104a. Fifth phantom 104e includes a third curved surface 900, a second left side surface 901, a second right side surface 902, a second top surface 904, a second bottom surface 906, a second front surface 908, a second back surface 910, a scanning window 912, a first reflective plate 924, and a second reflective plate 926. Scanning window 912 may be flat, formed in either or both of second front surface 908 and/or second back surface 910, made of the PCAF material, and have dimensions of 6 cm in a horizontal direction and 11 cm in a vertical direction.

A fifth edge 914 is formed to delineate a transition between second top surface 904 and second front surface 908. A sixth edge 918 is formed to delineate a transition between second top surface 904 and second back surface 910. A fifth curved edge 916 is formed in fifth edge 914 to have a fifth radius of curvature that is defined in a plane perpendicular to second top surface 904 and generally parallel to second front surface 908. A sixth curved edge 920 is formed in sixth edge 918 to have a sixth radius of curvature that is defined in a plane perpendicular to second top surface 904 and generally parallel to second back surface 910. Third curved surface 900 is formed in second top surface 904 and extends between fifth curved edge 916 and sixth curved edge 920. In an alternative embodiment, third curved surface 900 may be stepped in a manner similar to that shown with reference to stepped scanning surface 600. For illustration, the fifth radius of curvature may be 3 cm and the sixth radius of curvature may be 7 cm and third curved surface 900 may have a length of 22 cm.

Instead of fibers fifth phantom 104e includes a plurality of anechoic spheres 922 randomly distributed within the tissue mimicking material and bounded by a second boundary 928. For illustration, fifth phantom 104e may be designed for use with transducer 106 operating in the two to seven MHz frequency range though other frequency ranges may be used. Based on the resolution associated with transducer 106 operating in this frequency range, the plurality of anechoic spheres 922 may be four millimeters (mm) in diameter. The plurality of anechoic spheres 922 all have the same diameter and are low echo level relative to the tissue mimicking material. The density of the distribution of the plurality of anechoic spheres 922 within the tissue mimicking material may be one 4 mm diameter anechoic sphere per cubic centimeter. The plurality of anechoic spheres 922 and the tissue mimicking material surrounding them may be selected to have a density of 1.04 grams/millimeter, a propagation speed of 1540 meters/second, and an attenuation coefficient slope of 0.5 or 0.7 decibel(dB)/cm/MHz. The tissue mimicking material may have a frequency-dependent backscatter coefficient or "echogenicity" typical of tissue over the frequency range selected while the backscatter coefficient of the plurality of anechoic spheres 922 is more than 30 dB below that of the tissue mimicking material, thus simulating a cyst.

First reflective plate 924 and second reflective plate 926 form two parallel surfaces of the four surfaces that form second boundary 928. First reflective plate 924 and second reflective plate 926 extend generally parallel to second left side surface 901 and second right side surface 902, respectively, and generally perpendicular to second top surface 904, second bottom surface 906, second front surface 908, and second back surface 910. First reflective plate 924 and second reflective plate 926 may be used in a similar manner with the other phantoms described herein. For illustration, first reflective plate 924 and second reflective plate 926 may be formed of 3-6 mm thick stainless steel. As another example, first reflective plate 924 and second reflective plate 926 may be formed of 3-6 mm thick plate glass. As another example, first reflective plate 924 and second reflective plate 926 may be formed of 3-6 mm thick alumina (Al$_2$O$_3$) plate. Other materials include those formed from aluminum nitride, silicon carbide, Beramic 995, Beramic Z, and beryllium.

Merely for illustration, second boundary 928 may be 22 cm in a vertical direction and 12 cm in a horizontal direction. Second left side surface 901, second right side surface 902, second top surface 904, second bottom surface 906, second front surface 908, second back surface 910 may have various widths and may be formed of one or more layers of material. For illustration, a second width 930 may be approximately one cm.

Figure 10A:
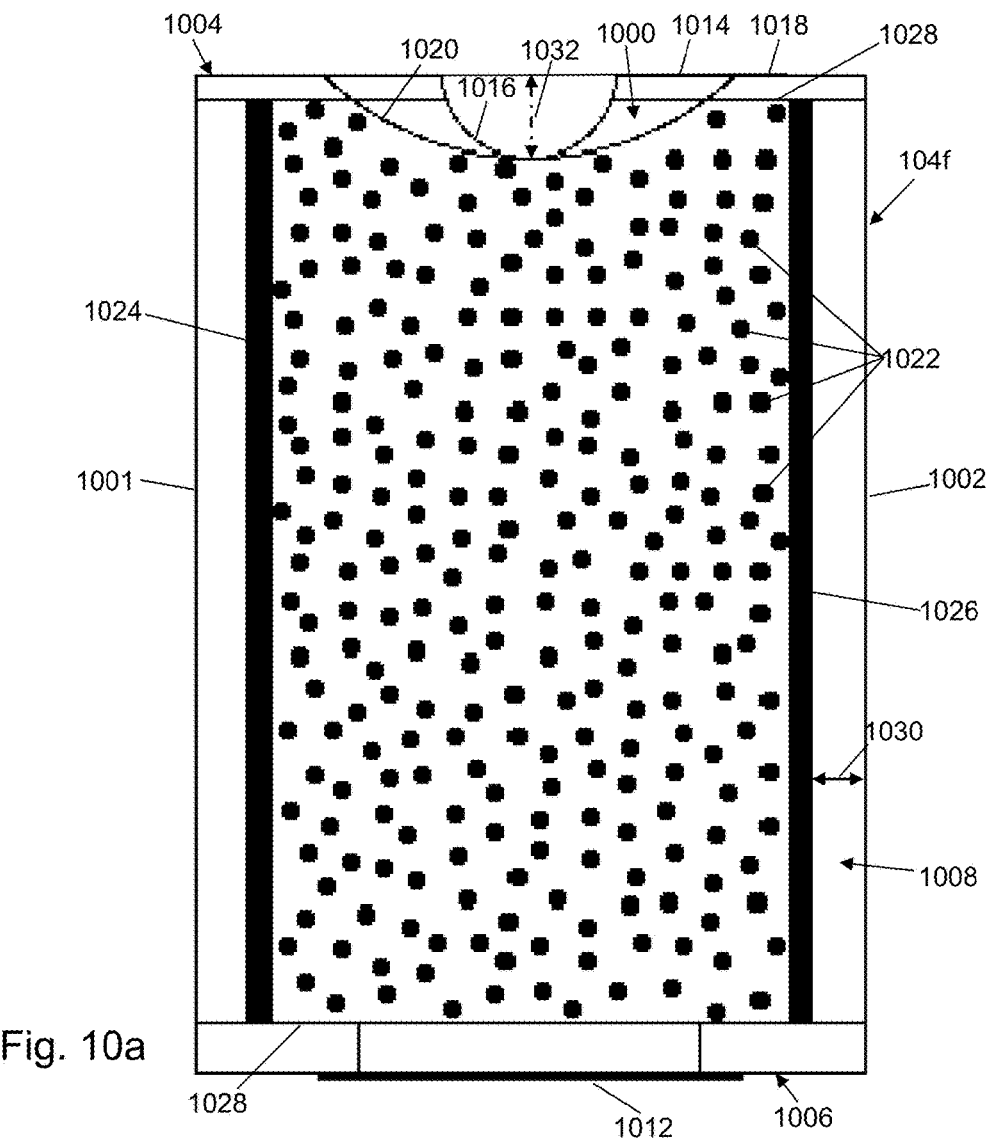
FIG. 10a depicts a front schematic view of a fourth phantom for use with the ultrasound system of FIG. 1 in accordance with a fourth illustrative embodiment.
Figure 10B:
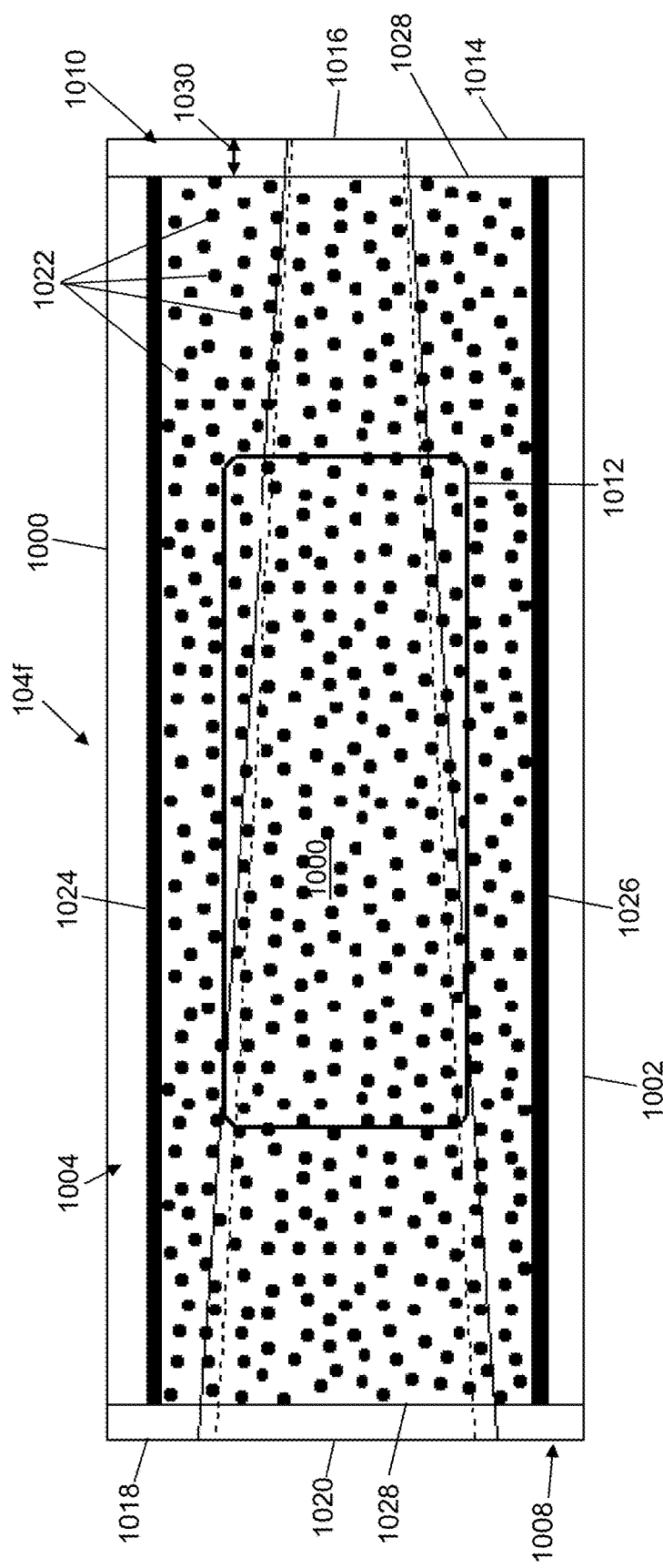

With reference to FIGS. 10a-10b, a sixth phantom 104f is shown in accordance with a fourth illustrative embodiment. Sixth phantom 104f is structurally similar to fifth phantom 104e. Sixth phantom 104f includes a fourth curved surface 1000, a third left side surface 1001, a third right side surface 1002, a third top surface 1004, a third bottom surface 1006, a third front surface 1008, a third back surface 1010, a second scanning window 1012, a third reflective plate 1024, and a fourth reflective plate 1026. Second scanning window 1012 may be flat, formed in either or both of third front surface 1008 and/or third back surface 1010, made of the PCAF material, and have dimensions of four cm in a horizontal direction and eleven cm in a vertical direction.

A seventh edge 1014 is formed to delineate a transition between third top surface 1004 and third front surface 1008. An eighth edge 1018 is formed to delineate a transition between third top surface 1004 and third back surface 1010. A seventh curved edge 1016 is formed in seventh edge 1014 to have a seventh radius of curvature that is defined in a plane perpendicular to third top surface 1004 and generally parallel to third front surface 1008. An eighth curved edge 1020 is formed in eighth edge 1018 to have a eighth radius of curvature that is defined in a plane perpendicular to third top surface 1004 and generally parallel to third back surface 1010. Fourth curved surface 1000 is formed in third top surface 1004 and extends between seventh curved edge 1016 and eighth curved edge 1020. In an alternative embodiment, fourth curved surface 1000 may be stepped in a manner similar to that shown with reference to stepped scanning surface 600. For illustration, the seventh radius of curvature may be 1 cm and the eighth radius of curvature may be 3.5 cm and fourth curved surface 1000 may have a length of 20 cm. A depth 1032 of fourth curved surface 1000 is constant between seventh curved edge 1016 and eighth curved edge 1020 and is parallel to third top surface 1004 to allow a translator on top of sixth phantom 104f to provide incremental translation of transducer 106 affixed on the translator i.e., to increment in steps parallel to third top surface 1004 of sixth phantom 104f. For illustration, depth 1032 may be one cm.

In another illustrative embodiment of sixth phantom 104f, the seventh radius of curvature may be 0.5 cm. For illustration, depth 1032 may be 1.5 cm.

Instead of fibers sixth phantom 104f includes a second plurality of anechoic spheres 1022 randomly distributed within the tissue mimicking material and bounded by a third boundary 1028. For illustration, sixth phantom 104f may be designed for use with transducer 106 operating in the seven to fifteen MHz frequency range though other frequency ranges may be used. Based on the resolution associated with transducer 106 operating in this frequency range, the second plurality of anechoic spheres 1022 may be two mm in diameter. The second plurality of anechoic spheres 1022 all have the same diameter and are low echo level relative to the tissue mimicking material. The density of the distribution of the second plurality of anechoic spheres 1022 within the tissue mimicking material may be eight 2 mm diameter anechoic spheres per cubic centimeter. The second plurality of anechoic spheres 1022 and the tissue mimicking material may be selected to have a density of 1.04 grams/millimeter, a propagation speed of 1540 meters/second, and an attenuation coefficient slope of 0.5 or 0.7 dB/cm/MHz. The tissue mimicking material may have a frequency-dependent backscatter coefficient or "echogenicity" of soft tissue over the frequency range selected while the backscatter coefficient of the second plurality of anechoic spheres 1022 is more than 30 dB below that of the tissue mimicking material, thus simulating a cyst.

Third reflective plate 1024 and fourth reflective plate 1026 form two parallel surfaces of the four surfaces that form third boundary 1028. Third reflective plate 1024 and fourth reflective plate 1026 extend generally parallel to third left side surface 1001 and third right side surface 1002, respectively, and generally perpendicular to third top surface 1004, third bottom surface 1006, third front surface 1008, and third back surface 1010. Third reflective plate 1024 and fourth reflective plate 1026 may be used in a similar manner with the other phantoms described herein. For illustration, third reflective plate 1024 and fourth reflective plate 1026 may be formed of 3 to 6 mm thick plate glass. Other reflective materials may be used for the reflective plates based on a desired cost and weight and any other manufacturing constraints.

Merely for illustration, third boundary 1028 may be 20 cm in a vertical direction and 6 cm in a horizontal direction. Third left side surface 1001, third right side surface 1002, third top surface 1004, third bottom surface 1006, third front surface 1008, third back surface 1010 may have various widths and may be formed of one or more layers of material. For illustration, third width 1030 may be approximately six mm except in third top surface 1004. In third top surface 1004, third width 1030 may be three mm.

Fifth phantom 104e and sixth phantom 104f incorporate the curved surfaces for imaging performance testing of any curved, linear or phased array transducer as described with reference to FIGS. 3-8c and are used for the determination of lesion signal-to-noise ratios (LSNR's) over the entire field of view of transducer 106. The size of fifth phantom 104e and sixth phantom 104f is greatly reduced by inclusion of the two parallel reflective plates. The angles of incidence of ultrasound beams exceed a critical angle resulting in fifth phantom 104e and sixth phantom 104f displaying the entire field of view for any curved or phased array transducer.

Figure 11:
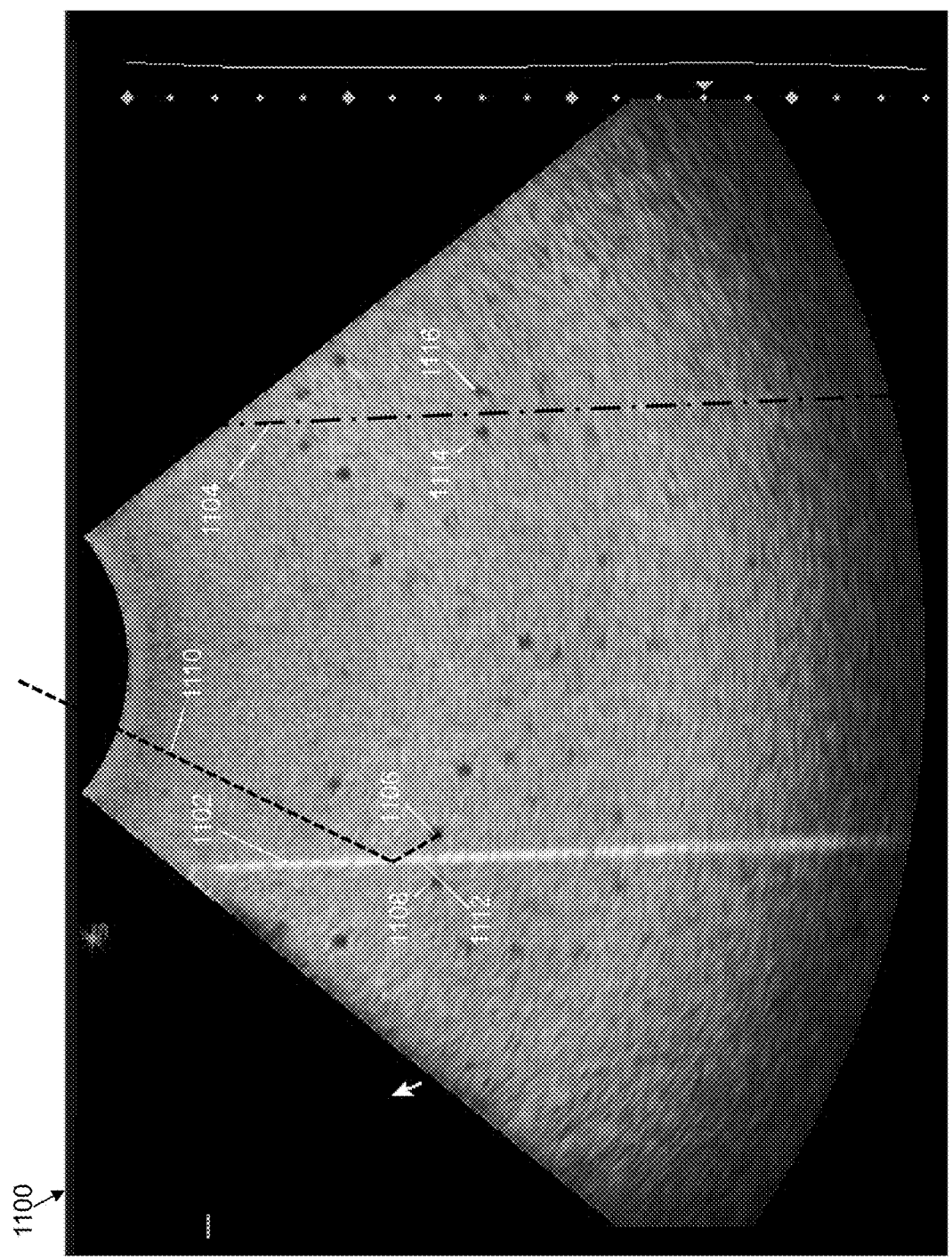

With reference to FIG. 11, a second image 1100 taken using transducer 106 using fifth phantom 104e of FIGS. 9a and 9b is shown. First reflective plate 924 formed of a flat alumina plate is shown as reflection 1102. Alumina has unusually high compression and shear ultrasound propagation speeds with critical angles of incidence relative to 1540 m/s of tissue-mimicking material of 8.3° and 14°, respectively; the Rayleigh critical angle is 15.7°. Thus, total internal reflection of compressional waves with no generation of shear or Rayleigh waves occurs for angles of incidence greater than 16°, which means that the specular, total internal reflection of compressional waves occurs for sector angles as large as 180°−32°=148°. 148° is larger than the sector angles of almost all convex arrays. The alumina, however, also gives rise to ultrasound reflections at its surface resulting in a bright line of echoes. Second reflective plate 926 was formed of plate glass which gives rise to minimal diffuse ultrasound scattering so that there is no apparent vertical line of echoes corresponding to its reflecting surface. The position of the reflecting plate 926 is indicated in second image 1100 at line 1104. First reflective plate 924 provides performance testing of the entire field of view for sector angles as large as 150° by simulating the existence of spheres beyond the volume actually containing spheres. Thus, the volume and weight of fifth phantom 104e is considerably reduced because of the reflecting surfaces. For example, a first beam 1110 emitted by transducer 106 was reflected from first reflective plate 924 along a second beam 1112. Second beam 1112 was reflected by a first sphere 1106 within fifth phantom 104e back in the direction of second beam 1112 and back again towards transducer 106 along first beam 1110. As a result, first sphere 1106 also appeared to be located at the location of a first ghost sphere 1108 thereby allowing a performance test of a field of view beyond boundary 928 of the tissue mimicking material. Similarly, a second ghost sphere 1116 was created by second sphere 1114 as a result of reflection of the sound waves by second reflective plate 926.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, the use of "and" or "or" is intended to include "and/or" unless specifically indicated otherwise. All dimensional measurements defined herein are approximate unless otherwise specified.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. An ultrasound phantom comprising:
   a container including a top surface, a bottom surface opposite the top surface, and a wall mounted between the top surface and the bottom surface to form the container;
   a boundary formed within the container and configured to hold a tissue mimicking material; and
   a curved scanning surface formed in the top surface to extend downwards from the top surface in a direction towards an interior of the container, wherein the curved scanning surface is shaped to support translation perpendicular to an image plane of an application end of an ultrasound transducer along at least a portion of an axis extending between a first location on the curved scanning surface and a second location on the curved scanning surface.

2. The ultrasound phantom of claim 1, wherein the curved scanning surface has a first radius of curvature at the first location in a range from 0.1 centimeters (cm) to ten cm, inclusive.

3. The ultrasound phantom of claim 2, wherein the curved scanning surface has a second radius of curvature at the second location in a range from 0.1 centimeters (cm) to ten cm, inclusive.

4. The ultrasound phantom of claim 3, wherein the first radius of curvature and the second radius of curvature are different.

5. The ultrasound phantom of claim 1, wherein a radius of curvature of the curved scanning surface varies continuously between the first location and the second location.

6. The ultrasound phantom of claim 1, wherein a radius of curvature of the curved scanning surface varies in discrete steps between the first location and the second location.

7. The ultrasound phantom of claim 6, wherein the radii of curvature of the discrete steps vary monotonically between the first location and the second location.

8. The ultrasound phantom of claim 1, wherein the curved scanning surface is covered with a plastic-coated aluminum foil.

9. The ultrasound phantom of claim 1, further comprising a second curved scanning surface formed in the bottom surface in a direction towards the interior of the container.

10. The ultrasound phantom of claim 9, wherein a radius of curvature of the curved scanning surface and a radius of curvature of the second curved scanning surface have the same value at a third location on the curved scanning surface and a fourth location on the second curved scanning surface.

11. The ultrasound phantom of claim 1, further comprising a plurality of fibers suspended in the tissue mimicking material.

12. The ultrasound phantom of claim 1, a flat scanning window mounted within the wall, wherein the wall comprises a right surface, a left surface, a front surface mounted between the right surface and the left surface, and a back surface mounted between the right surface and the left surface and generally opposite the front surface, wherein the front surface and the back surface are perpendicular to the axis, and further wherein the flat scanning window is mounted within the front surface or the back surface.

13. The ultrasound phantom of claim 12, wherein the tissue mimicking material is in direct contact with the flat scanning window or the left surface.

14. The ultrasound phantom of claim 12, further comprising a second flat scanning window mounted within the right surface.

15. The ultrasound phantom of claim 1, further comprising a plurality of anechoic spheres randomly distributed in the tissue mimicking material.

16. The ultrasound phantom of claim 15, further comprising:
   a first flat reflective plate; and
   a second flat reflective plate; wherein the first flat reflective plate and the second flat reflective plate are mounted adjacent to the boundary and in contact with the tissue mimicking material and are configured to specularly reflect an incident compressional ultrasound beam transmitted into the tissue mimicking material from the ultrasound transducer back into the tissue mimicking material with no mode conversion from compressional to either shear or Rayleigh waves.

17. The ultrasound phantom of claim 16, wherein the first flat reflective plate is formed of a material selected from the group consisting of glass, stainless steel, alumina, aluminum nitride, silicon carbide, Beramic 995, Beramic Z, and beryllium.

18. The ultrasound phantom of claim 16, wherein the wall comprises a right surface, a left surface, a front surface mounted between the right surface and the left surface, and a back surface mounted between the right surface and the left surface and generally opposite the front surface, wherein the front surface and the back surface are perpendicular to the axis, and further wherein the first flat reflective plate is mounted in a third plane parallel to the right surface and the second flat reflective plate is mounted in a fourth plane parallel to the left surface.

19. The ultrasound phantom of claim 18, further comprising a flat scanning window mounted within the front surface or within the back surface.

20. The ultrasound phantom of claim 1, wherein the wall comprises a right surface, a left surface, a front surface mounted between the right surface and the left surface, and a back surface mounted between the right surface and the left surface and generally opposite the front surface.

* * * * *